(12) United States Patent
Muramatsu et al.

(10) Patent No.: US 11,653,902 B2
(45) Date of Patent: May 23, 2023

(54) ULTRASOUND IMAGE DIAGNOSTIC APPARATUS AND POWER SUPPLY CONTROL METHOD

(71) Applicant: Konica Minolta, Inc., Tokyo (JP)

(72) Inventors: Yuki Muramatsu, Saitama (JP); Kazuya Osada, Tokyo (JP); Yasuhiro Nakamura, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 97 days.

(21) Appl. No.: 17/213,175

(22) Filed: Mar. 25, 2021

(65) Prior Publication Data

US 2021/0315548 A1  Oct. 14, 2021

(30) Foreign Application Priority Data

Apr. 9, 2020 (JP) ............................. JP2020-070357

(51) Int. Cl.
*A61B 8/00* (2006.01)
*H02J 7/00* (2006.01)

(52) U.S. Cl.
CPC .............. *A61B 8/56* (2013.01); *H02J 7/0063* (2013.01)

(58) Field of Classification Search
CPC .. A61B 8/56; A61B 8/54; H02J 7/0063; H02J 2310/23; H02J 7/0032
See application file for complete search history.

(56) References Cited

U.S. PATENT DOCUMENTS

2018/0325495 A1* 11/2018 Nakamura ............. G16H 30/40

FOREIGN PATENT DOCUMENTS

| JP | H05261096 A | * 3/1992 | ............. G16H 30/40 |
| JP | H05-261096 A | 10/1993 | |

* cited by examiner

*Primary Examiner* — Yi-Shan Yang
*Assistant Examiner* — Alexei Bykhovski
(74) *Attorney, Agent, or Firm* — Lucas & Mercanti, LLP

(57) ABSTRACT

An ultrasound image diagnostic apparatus includes: a power source control section that supplies power to a power source section which performs supply of power to each part of the ultrasound image diagnostic apparatus; a battery that supplies the power to the power source control section: an external power supply section that supplies, to the power source control section, the power supplied from outside of the ultrasound image diagnostic apparatus; and a power supply control section that controls supply of power from the battery and the external power supply section to the power source control section based on an operation state of the ultrasound image diagnostic apparatus and the presence or absence of the power supplied from the external power supply section.

9 Claims, 5 Drawing Sheets

ULTRASOUND IMAGE DIAGNOSTIC APPARATUS AND POWER SUPPLY CONTROL METHOD

CROSS REFERENCE TO RELATED APPLICATIONS

The entire disclosure of Japanese Patent Application No. 2020-70357 filed on Apr. 9, 2020 is incorporated herein by reference in its entirety.

BACKGROUND

Technological Field

The present disclosure relates to an ultrasound image diagnostic apparatus and a power supply control method.

Description of Related Art

Conventionally an ultrasound image diagnostic apparatus has been known, which performs transmission and reception of ultrasound to and from a subject such as a living body with an ultrasound probe, generates ultrasound image data based on a signal obtained from the received ultrasound, and displays an ultrasound image based on the ultrasound image data on an image display device. Ultrasound image diagnosis by the ultrasound image diagnostic apparatus can be carried out repeatedly, because a state of heartbeat and movement of a fetus and the like can be obtained in real time by a simple operation to put the ultrasound probe to a body surface of the subject; in addition, it is non-invasive and has high safety.

Japanese Patent Application Laid-Open No. H5-261096 discloses an ultrasound image diagnostic apparatus including a battery and an Alternating Current (AC)-Direct Current (DC) converter. The AC-DC converter converts source power supplied from the outside such as a commercial power source and supplies the source power to a power supply section which is for supplying power to each part of the ultrasound image diagnostic apparatus. Further, the AC-DC converter also charges the battery. In a condition where no external power source is available, the battery supplies the source power to the power supply section. Under an ordinary environment of a medical examination, ultrasound image diagnostic apparatus is often operated on commercial power source, but it may be operated by a battery, because the commercial power source may not be available in some areas, such as outdoors. After the operation using the battery, the battery is charged by connecting it to the commercial power source.

In recent years, as this type of ultrasound image diagnostic apparatus, an apparatus is known, which, in a condition where no external power source is available, supplies standby power from a battery to a power source control circuit (hereinafter, referred to as a "power source control section") that supplies power to a power source section for the next activation even in a shutdown state.

SUMMARY

However, in a condition where no external power source is available, when a shutdown state of the ultrasound image diagnostic apparatus becomes longer, the amount of standby power supplied to a power source control section becomes larger, which causes an increase in power consumption of the battery. In currently prevailing ultrasound image diagnostic apparatuses, the batteries drain quickly, and, for example, during the Friday night on weekends to the Monday morning, the standby power is continuously supplied to the power source control sections. This result in that the power consumption of the battery increases, and a remaining charge amount is greatly reduced. Consequently, an attempt to perform a medical examination using the ultrasound image diagnostic apparatus on the Monday morning results in running out of power of the battery during the course of the examination in some cases. Thus, a technique of reducing the amount of the standby power supplied to the power source control section in the shutdown state of the ultrasound image diagnostic apparatus to reduce the power consumption of the battery has been desired.

An object of the present disclosure is to provide an ultrasound image diagnostic apparatus and a power supply control method capable of reducing power consumption of a battery in a shutdown state.

To achieve at least one of the abovementioned objects, an ultrasound image diagnostic apparatus reflecting one aspect of the present invention includes:

a power source control section that supplies power to a power source section which performs supply of power to each part of the ultrasound image diagnostic apparatus;

a battery that supplies the power to the power source control section;

an external power supply section that supplies, to the power source control section, the power supplied from outside of the ultrasound image diagnostic apparatus; and a power supply control section that controls supply of power from the battery and the external power supply section to the power source control section based on an operation state of the ultrasound image diagnostic apparatus and a presence or absence of the power supplied from the external power supply section.

A power supply control method reflecting another aspect of the present invention for an ultrasound image diagnostic apparatus, the ultrasound image diagnostic apparatus including:

a power source control section that supplies power to a power source section which performs supply of power to each section of the ultrasound image diagnostic apparatus; a battery that supplies the power to the power source control section; and an external power supply section that supplies, to the power source control section, the power supplied from outside of the ultrasound image diagnostic apparatus, the power supply control method includes: controlling supply of power from the battery and the external power supply section to the power source control section based on an operation state of the ultrasound image diagnostic apparatus and a presence or absence of the power supplied from the external power supply section.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

Figure 1:
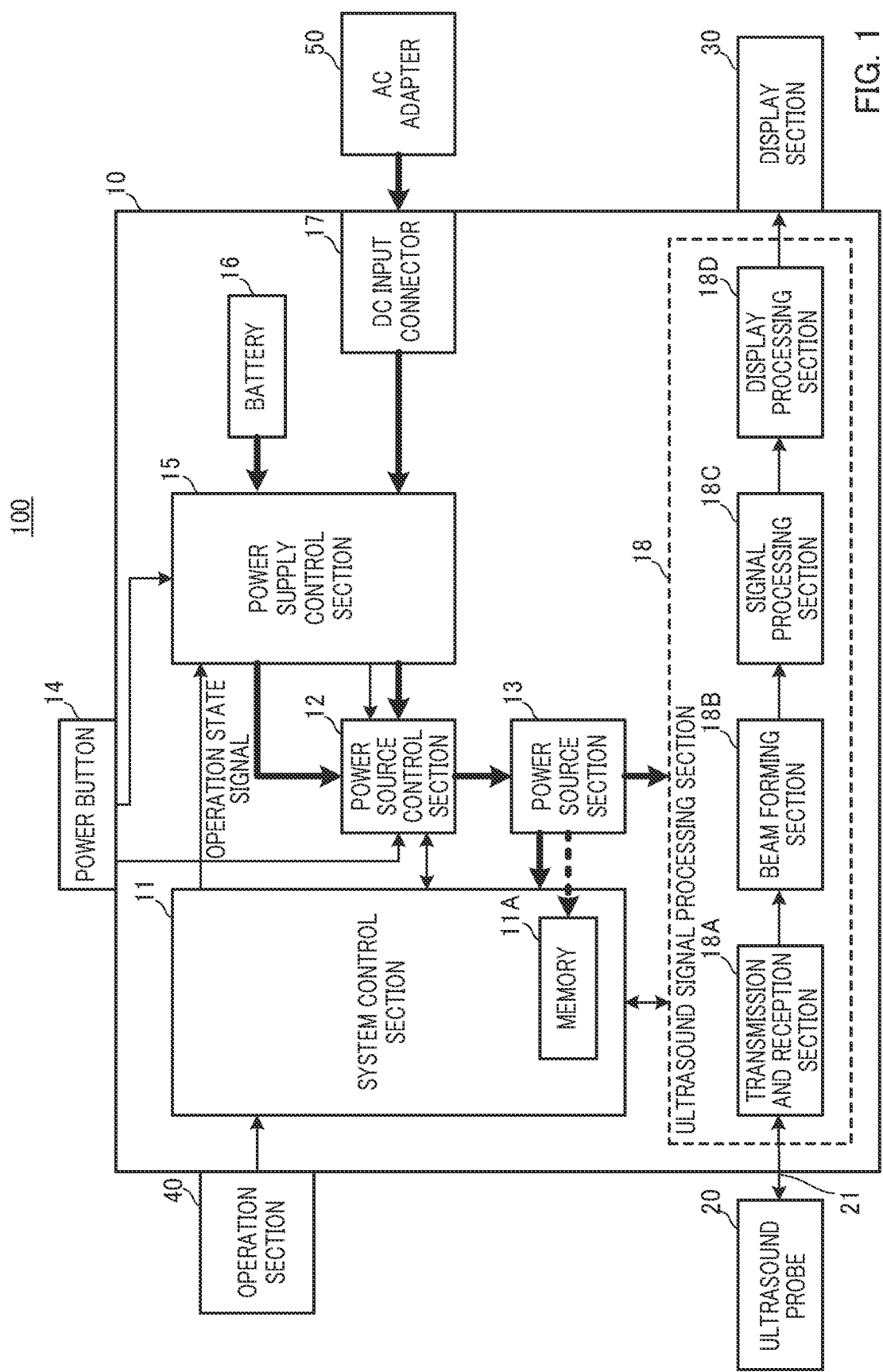
FIG. 1 is a block diagram illustrating a functional configuration of an ultrasound image diagnostic apparatus.

Hereinafter, a description will be given of ultrasound image diagnostic apparatus 100 according to the present embodiment in detail with reference to the drawings. FIG. 1 is a block diagram illustrating a functional configuration of ultrasound image diagnostic apparatus 100.

Ultrasound image diagnostic apparatus 100 is a diagnostic apparatus portable for a user (e.g., a clinical technician such as a doctor or technologist) which is used, for example, in a medical institute having a commercial power source such as a hospital or outdoors without the commercial power source. As illustrated in FIG. 1, ultrasound image diagnostic apparatus 100 includes casing 10, ultrasound probe 20, display section 30, operation section 40, and AC adapter 50.

Ultrasound probe 20 transmits ultrasound (transmission ultrasound) into a subject such as a living body of a patient (not illustrated) and receives reception ultrasound including reflected ultrasound reflected inside of the subject and scattered ultrasound. Casing 10 is connected to ultrasound probe 20 via cable 21 and causes ultrasound probe 20 to transmit the transmission ultrasound into the subject by transmitting a drive signal (an electric signal) to ultrasound probe 20. In addition, casing 10 images an internal state of the subject as an ultrasound image based on a reception signal (an electric signal) generated by ultrasound probe 20 in accordance with the reception ultrasound received by ultrasound probe 20 from the subject.

Transducers of ultrasound probe 20 (not illustrated) are arranged, for example, in a one-dimensional array in an orientation direction. In the present embodiment, for example, ultrasound probe 20 having 192 transducers is used. Note that, the transducers may be arranged in a two-dimensional array. The number of transducers can be set optionally. Besides, ultrasound probe 20 may adopt either an electronic scanning system or a mechanical scanning system, and may adopt any of a linear scanning system, a sector scanning system, or a convex scanning system.

As illustrated in FIG. 1, casing 10 includes system control section 11, power source control section 12, power source section 13, power button 14, power supply control section 15, battery 16, DC input connector 17 (functions as an "external power supply" of the present invention), and ultrasound signal processing section 18. System control section 11 includes memory 11A, which is a volatile memory.

Ultrasound signal processing section 18 includes transmission and reception section 18A, beam forming section 18B, signal processing section 18C, and display processing section 18D.

Operation section 40 includes, for example, various switches, buttons, trackballs, mouses, keyboards and/or the like to input various commands such as an instruction to start an inspection of a subject, and/or data such as measurement conditions or information on the subject. Operation section 40 outputs operation information to system control section 11 according to operation input. In particular, in a case of termination of ultrasound image diagnostic apparatus 100, operation section 40 receives, from the user, input of execution of the termination and selection information on a termination method (shutdown or standby).

Transmission and reception section 18A functions as a transmission section that generates, according to a drive voltage (drive voltage value) from system control section 11, a drive signal (the electric signal) corresponding to the drive voltage and supplies the drive signal to ultrasound probe 20 via cable 21 to generate the transmission ultrasound.

As the transmission section, transmission and reception section 18A includes, for example, a clock generation circuit, a delay circuit, and a pulse generation circuit. The clock generation circuit is for generating a clock signal which determines a transmission timing and/or a transmission frequency of the drive signal. The delay circuit is for converging transmission beams constituted of transmission ultrasound by setting delay times for transmission timings of the drive signals respectively for individual paths corresponding to the transducers and delaying transmission of the drive signals by the set delay times. The pulse generation circuit is for generating a pulse signal as the drive signal at a predetermined frequency.

Transmission and reception section 18A having the above-mentioned configuration drives, for example, a contiguous part (e.g., 64 pieces) of a plurality of transducers (e.g., 192 pieces) arranged in ultrasound probe 20 to generate the transmission ultrasound. Thus, transmission and reception section 18A performs scanning (scan) by shifting the transducers to be driven in the orientation direction at each time the transmission ultrasound is generated. Accordingly, ultrasound probe 20 performs an operation of ultrasound transmission and reception according to the drive signal from transmission and reception section 18A.

In addition, transmission and reception section 18A functions as a reception section that receives the reception signal (the electric signal) from ultrasound probe 20 via cable 21, in accordance with the control of system control section 11. Transmission and reception section 18A outputs the reception signal of each transducer of ultrasound probe 20.

Beam forming section 18B generates sound ray data by strengthening the reception signals of the respective transducers input from transmission and reception section 18A, in accordance with the control of system control section 11. Beam forming section 18B includes, for example, am amplifier, an Analog to Digital (A/D) conversion circuit, and a phasing addition circuit. The amplifier is a circuit for amplifying the reception signal at a predetermined amplification factor, for each of individual paths respectively corresponding to the transducers. The A/D conversion circuit is for A/D converting the amplified reception signal. The phasing addition circuit is for providing the A/D converted reception signals, for the individual paths respectively corresponding to the transducers, with delay times to adjust the time phases, and adding up the time phases, thereby generating the sound ray data.

Signal processing section 18C generates a Brightness (B)-mode image data by performing envelope detection processing and/or a logarithmic amplification for the sound ray data input from beam forming section 18B, and adjusting a dynamic range and/or a gain to perform a luminance conversion, in accordance with the control of system control section 11. The B-mode image data is an image that presents intensity of the reception signal with a luminance Signal processing section 18C can generate, in addition to the B-mode image data for B-mode of a diagnostic mode, the ultrasound image data of other diagnostic modes, such as an Amplitude (A)-mode, a Motion (M)-mode, a pulse Doppler mode, and a color Doppler mode.

In addition, signal processing section 18C includes an image memory section (not illustrated) configured of a semiconductor memory such as a Dynamic Random Access Memory (DRAM). Signal processing section 18C, in accordance with the control of system control section 11, stores the generated B-mode image data in the image memory section in units of frames and outputs the B-mode image data as an image data for each frame.

Display processing section 18D performs, in accordance with the control of system control section 11, coordinate transformation of the image data of the frame input from signal processing section 18C to convert the image data to an image signal, and outputs the image signal to display section 30.

Display devices such as Liquid Crystal Display (LCD), a Cathode-Ray Tube display (CRT), an organic Electronic Luminescence (EL) display, an inorganic EL display, and a plasma display are applicable to display section 30. Display section 30 displays, for example, an ultrasound image according to the image signal input from display processing section 18D, in accordance with the control of system control section 11 via ultrasound signal processing section 18. In particular, in a case of termination of ultrasound image diagnostic apparatus 100, display section 30 displays display screen information that receives input of an execution of the termination and selection of a termination method (shutdown or standby) from a user.

System control section 11 includes, for example, a Central Processing Unit (CPU), a Read Only Memory (ROM), and memory 11A, reads out various processing programs, such as a system program stored in the ROM and loads the read programs into memory 11A, and, according to the loaded programs, controls each section of ultrasound image diagnostic apparatus 100. The ROM is configured of, for example, a nonvolatile memory such as a semiconductor and stores the system program corresponding to ultrasound image diagnostic apparatus 100, various processing programs executable on the system program, and/or various data such as a gamma table, and the like. These programs are stored in a form of computer-readable program code, and the CPU successively executes an operation according to the program code. Memory 11A is a volatile storage section such as a Random Access Memory (RAM) and forms a work area that temporarily stores various programs executed by the CPU and data relating to these programs.

In a case where an operation state of ultrasound image diagnostic apparatus 100 transitions from an active state to a standby state or a shutdown state, system control section 11 outputs an operation state signal indicating the operation state after the transition (the standby state or the shutdown state) to power supply control section 15.

Power supply control section 15 controls a supply of power from battery 16 and DC input connector 17 to power source control section 12 based on the operation state of ultrasound image diagnostic apparatus 100 (e.g., the active state, the standby state, or the shutdown state) and the presence or absence of power supplied from DC input connector 17.

Power supply control section 15 determines the presence or absence of the power supplied from DC input connector 17. By way of example, power supply control section 15 determines that the power supplied from DC input connector 17 is present when an amount of the power supplied from DC input connector 17 is not less than a predetermined value, and determines that the power supplied from DC input connector 17 is absent when an amount of the power is less than a predetermined value.

Power supply control section 15 operates on receiving the power supplied from battery 16 or DC input connector 17. In the present embodiment, power supply control section 15 is a simple electric circuit configured of only a logic circuit, a transistor, a resistance and/or the like.

Power source control section 12 performs the following processing: supply of source power to power source section 13; standby for pressing power button 14, notification to system control section 11 of information on pressing of power button 14, and termination (standby, shutdown) or activation of ultrasound image diagnostic apparatus 100 according to system control section 11 in a case where the power is supplied from battery 16 or DC input connector 17 via power supply control section 15. In the present embodiment, power source control section 12 is a large scale integrated circuit configured to include an IC dedicated to the power source control. That is, the power consumption of power source control section 12 is larger than the power consumption of power supply control section 15.

Power source section 13 is a power source for supplying power to system control section 11, ultrasound signal processing section 18 (ultrasound probe 20, display section 30, operation section 40). In particular, in a case where the operation state of ultrasound image diagnostic apparatus 100 is the standby state, power source section 13 supplies power (standby power source) to memory 11A according to an instruction of power source control section 12. Power source section 13 may be configured of a regulator (a DC-DC converter, a series regulator). The regulator may be a circuit configured of a discrete part or may be configured of an IC or a circuit module.

Power button 14 is provided on a front surface of casing 10, receives a pressing operation input as an on/off operation of the power source from the user, and outputs an operation signal to power source control section 12 and power supply control section 15. An operation content to be received by power button 14 is an activation operation after termination (standby or shutdown) of ultrasound image diagnostic apparatus 100 or a termination (shutdown) operation while ultrasound image diagnostic apparatus 100 is active.

AC adapter 50 is electrically connected to a commercial power source, converts an alternating current of the input of the commercial power source to a direct current, and supplies the direct current after conversion as a source power to DC input connector 17, which is a connection destination of AC adaptor 50.

DC input connector 17 is an input connector provided on a front surface of casing 10 and provided for electrically connecting AC adapter 50. DC input connector 17 outputs the direct current (the source power) input from electrically connected AC adapter 50, to power supply control section 15.

Battery 16 is a secondary battery such as a lithium ion battery incorporated in casing 10, which is capable of charging power from AC adapter 50 and outputting (discharging) power to power supply control section 15.

Figure 2:
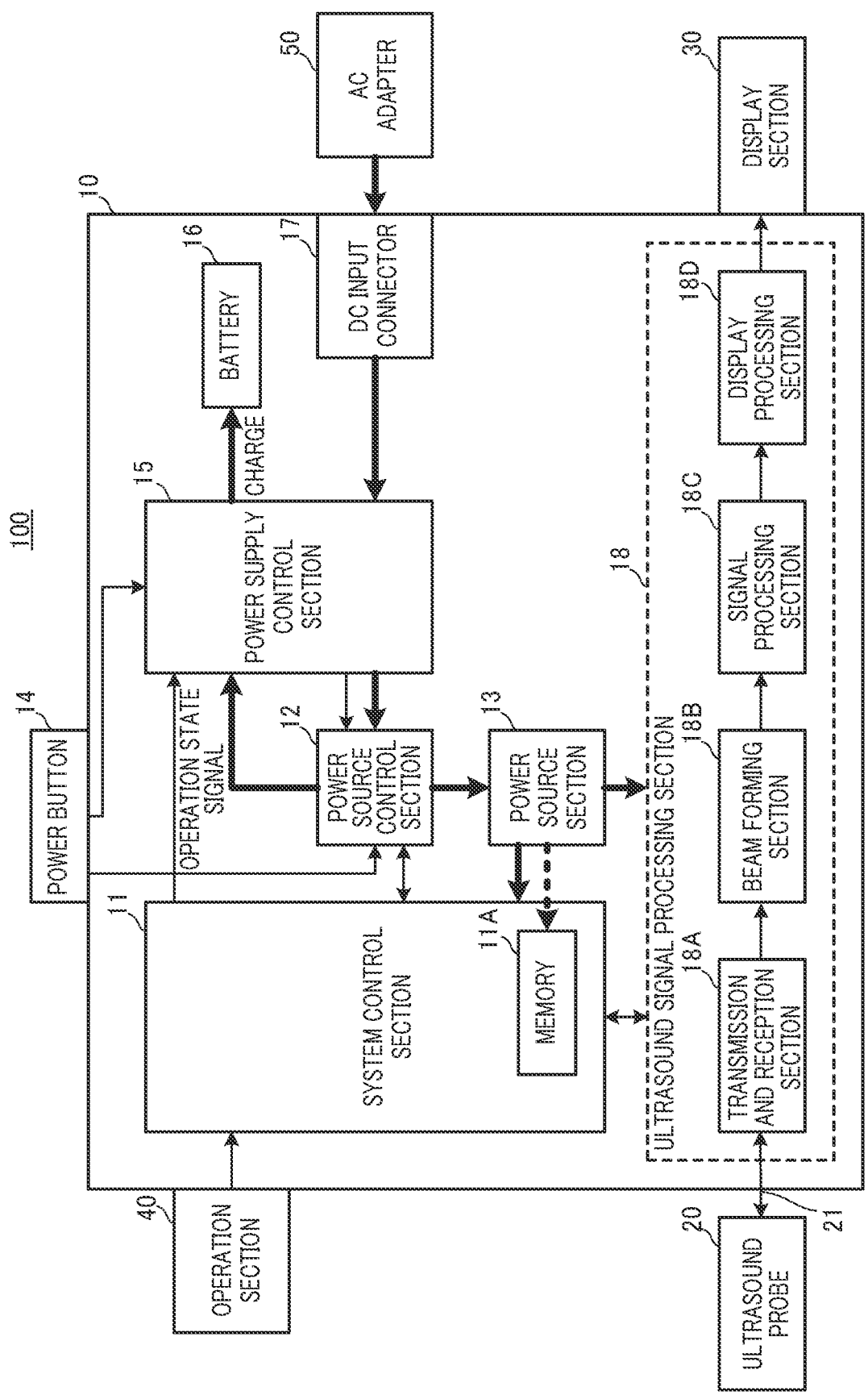
FIG. 2 is another block diagram illustrating the functional configuration of the ultrasound image diagnostic apparatus.

For each part of ultrasound image diagnostic apparatus 100, some or all of the functions of each functional block can be realized by a hardware circuit, such as an integrated circuit. The integrated circuit is, for example, a Large Scale Integration (LSI), and the may be referred to as an Integrated Circuit (IC), a system LSI, a super LSI, or an ultra LSI depending on a difference in the degree of integration. However, the technique of implementing an integrated circuit is not limited to the LSI and may be realized by using a dedicated circuit, a general-purpose processor, or may utilize a Field Programmable Gate Array (FPGA) or a reconfigurable processor capable of reconfiguring the connection and the setting of circuit cells disposed inside the LSI. In addition, some or all of the functions of each function block may be realized by software. In this case, the software is stored, for example, in a storage medium such as one or more ROMs, an optical disk, or a hard disk, and the software is executed by a computation processor Next, a description will be given of power supply control executed by power supply control section 15 with reference to FIGS. 2 to 5. FIG. 2 is a block diagram illustrating a functional configuration of ultrasound image diagnostic apparatus 100 in a case where an operation state of ultrasound image diagnostic apparatus 100 transitions from a shutdown state to an active state by a pressing operation of power button 14.

As illustrated in FIG. 2, power supply control section 15 receives an operation signal output from power button 14 and determines that an operation state of ultrasound image diagnostic apparatus 100 has transitioned from the shutdown state to the active state. Further, since AC adapter 50 is electrically connected to DC input connector 17, (i.e., since an amount of power supplied from DC input connector 17 is not less than a predetermined value), power supply control section 15 determines that the power supplied from DC input connector 17 is present. In accordance with the above determination results, power supply control section 15 causes the power from DC input connector 17 to be supplied to power source control section 12.

Specifically, power supply control section 15 receives the power supplied from DC input connector 17 and outputs the received power to power source control section 12. In addition, power supply control section 15 controls power source control section 12 to supply the power output from power supply control section 15 to power source section 13. Power source section 13 supplies the power supplied from power source control section 12 to system control section 11, ultrasound signal processing section 18 or the like. After that, for example, activation processing of ultrasound image diagnostic apparatus 100 is performed according to system control section 11.

Further, power supply control section 15 charges battery 16 by supplying, to battery 16, the power supplied from DC input connector 17. Specifically, power supply control section 15 controls power source control section 12 to supply the power output from power supply control section 15 to battery 16 via power supply control section 15 in a case where it is possible to charge battery 16. In the present embodiment, power source control section 12 has a charge control function of battery 16 and thereby is capable of monitoring a remaining charge amount and a state of battery 16. Thus, power source control section 12 determines that battery 16 can be charged when the remaining charge amount of battery 16 is not 100% (a full charge).

Figure 3:
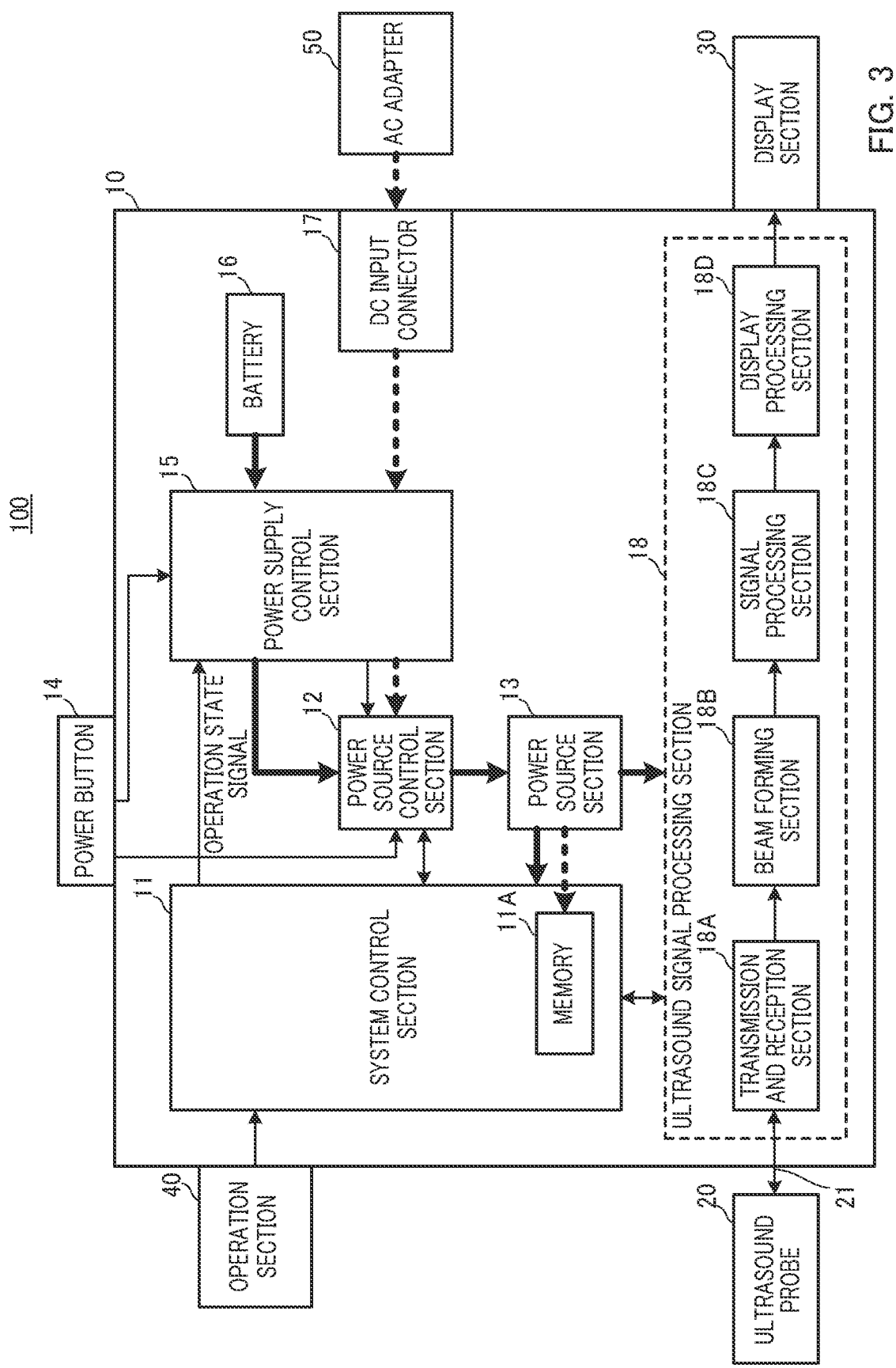
FIG. 3 is still another block diagram illustrating the functional configuration of the ultrasound image diagnostic apparatus.

FIG. 3 is a block diagram illustrating a functional configuration of ultrasound image diagnostic apparatus 100 in a case where an operation state of ultrasound image diagnostic apparatus 100 transitions from a shutdown state to an active state by a pressing operation of power button 14. However, unlike FIG. 2, AC adapter 50 is not electrically connected to DC input connector 17.

As illustrated in FIG. 3, power supply control section 15 receives an operation signal output from power button 14 and determines that an operation state of ultrasound image diagnostic apparatus 100 has transitioned from the shutdown state to the active state. Further, since AC adapter 50 is not electrically connected to DC input connector 17, (i.e., since an amount of power supplied from DC input connector 17 is less than a predetermined value), power supply control section 15 determines that the power supplied from DC input connector 17 is absent. In accordance with the above determination results, power supply control section 15 causes the power from battery 16 to be supplied to power source control section 12.

Specifically, power supply control section 15 receives the power supplied from battery 16 and outputs the received power to power source control section 12. In addition, power supply control section 15 controls power source control section 12 to supply the power output from power supply control section 15 to power source section 13. Power source section 13 supplies the power supplied from power source control section 12 to system control section 11, ultrasound signal processing section 18 and/or the like. After that, for example, activation processing of ultrasound image diagnostic apparatus 100 is performed according to system control section 11.

Figure 4:
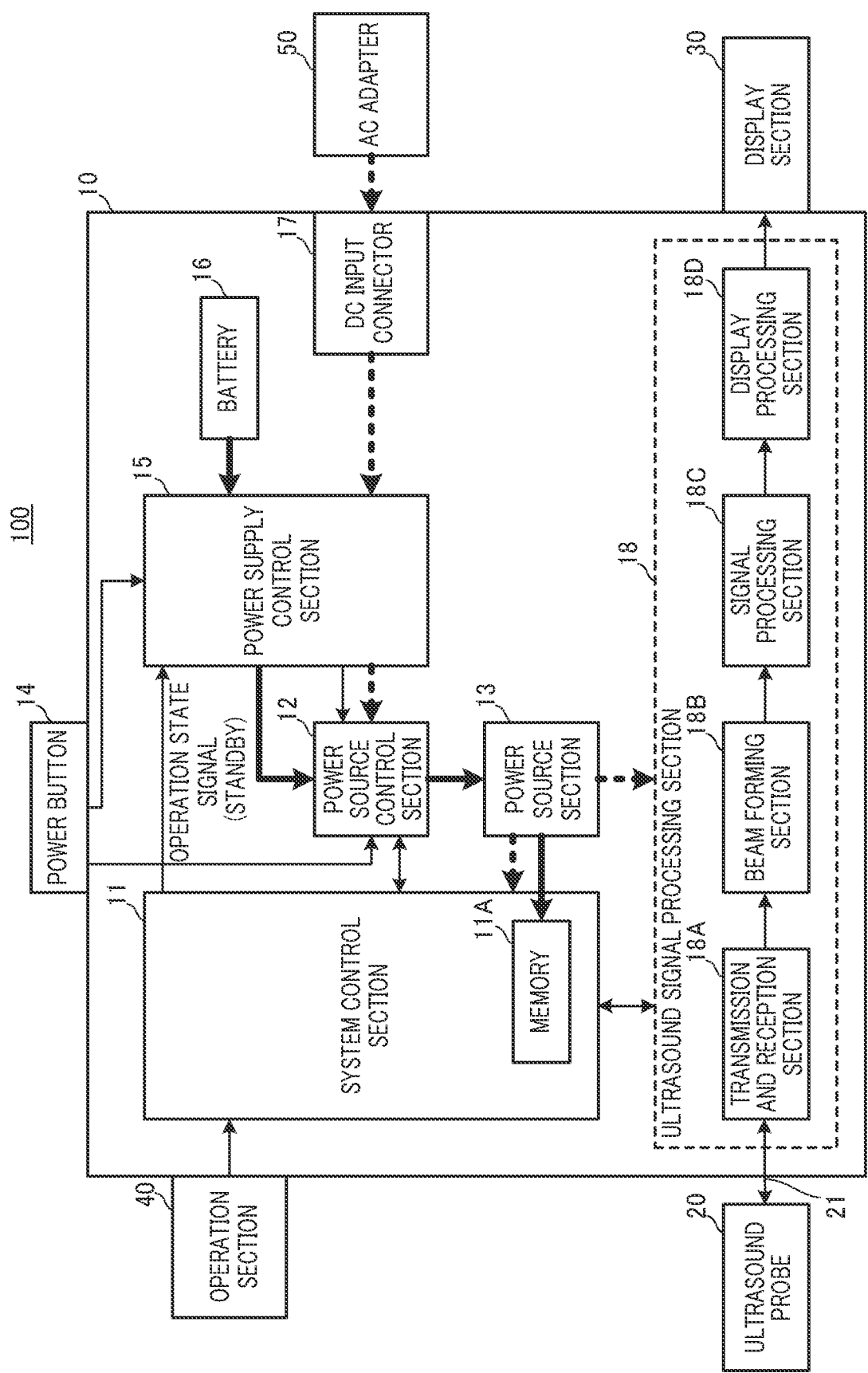
FIG. 4 is still another block diagram illustrating the functional configuration of the ultrasound image diagnostic apparatus.

FIG. 4 is a block diagram illustrating a functional configuration of ultrasound image diagnostic apparatus 100 in a case where an operation state of ultrasound image diagnostic apparatus 100 transitions from an active state to a standby state.

In ultrasound image diagnostic apparatus 100 in the active state, when receiving a termination instruction of ultrasound image diagnostic apparatus 100 from a user via operation section 40, system control section 11 displays display screen information on selection of termination methods of ultrasound image diagnostic apparatus 100 on display section 30. System control section 11 then receives selected input of the standby from the user via operation section 40, as the termination method of ultrasound image diagnostic apparatus 100.

As described above, when the display screen information on selection of termination methods is displayed on display section 30 during operation of ultrasound image diagnostic apparatus 100, and the standby is selectively input in order to, for example, temporarily stop ultrasound image diagnostic apparatus 100 for re-operating after an optional short time passes, system control section 11 brings power source control section 12 into the standby state. Further, system control section 11 outputs an operation state signal indicating the standby state as the operation state of ultrasound image diagnostic apparatus 100 to power supply control section 15.

Power supply control section 15 receives an operation state signal output from system control section 11 and determines that an operation state of ultrasound image diagnostic apparatus 100 has transitioned from the active state to the standby state. Further, since AC adapter 50 is not connected to DC input connector 17, (i.e., since an amount of power supplied from DC input connector 17 is less than a predetermined value), power supply control section 15 determines that the power supplied from DC input connector 17 is absent. In accordance with the above determination results, power supply control section 15 causes the power from battery 16 to be supplied to power source control section 12.

Specifically, power supply control section 15 receives the power supplied from battery 16, outputs the received power to power source control section 12, and enters the standby state capable of receiving an operation of power button 14 by using the power. In addition, power supply control section 15 controls power source control section 12 to supply the power output from power supply control section 15 to power source section 13. Power source section 13 supplies, to memory 11A, the power supplied from power source control section 12 and keeps the data stored in memory 11A. Terminating ultrasound image diagnostic apparatus 100 by selecting the standby enables keeping the data stored in memory 11A and resuming ultrasound image diagnostic apparatus 100 using the data after re-activation of ultrasound image diagnostic apparatus 100. After that, for example, termination (standby) processing of ultrasound image diagnostic apparatus 100 is performed according to system control section 11.

Figure 5:
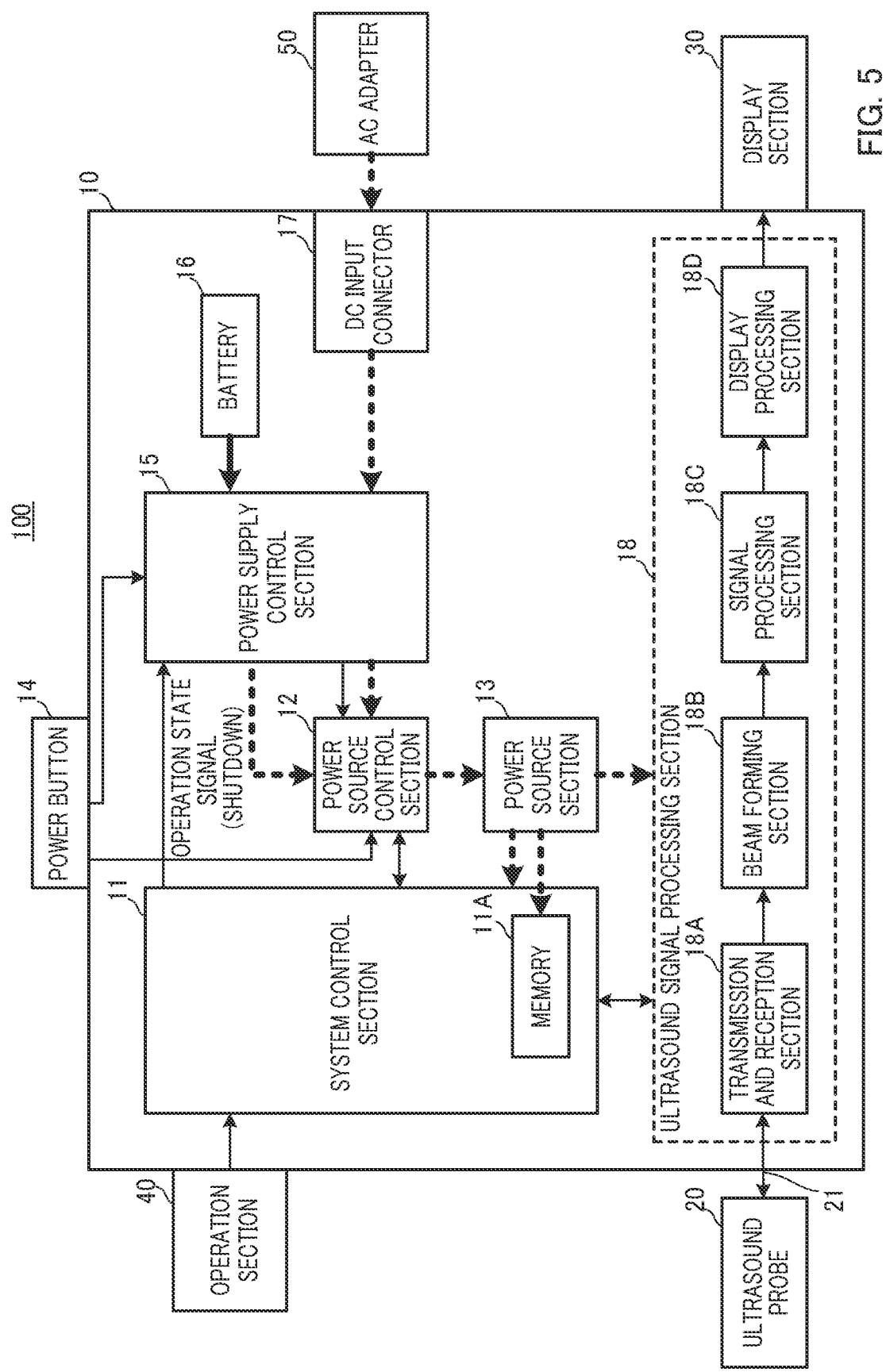
FIG. 5 is yet another block diagram illustrating the functional configuration of the ultrasound image diagnostic apparatus.

FIG. 5 is a block diagram illustrating a functional configuration of ultrasound image diagnostic apparatus 100 in a case where an operation state of ultrasound image diagnostic apparatus 100 transitions from an operation state to a shutdown state.

In ultrasound image diagnostic apparatus 100 in the active state, when receiving a termination instruction of ultrasound image diagnostic apparatus 100 from a user via operation section 40, system control section 11 displays display screen information on selection of termination methods of ultrasound image diagnostic apparatus 100 on display section 30. System control section 11 then receives selected input of the shutdown from the user via operation section 40, as the termination method of ultrasound image diagnostic apparatus 100.

As described above, when the display screen information on selection of termination methods is displayed on display section 30 during operation of ultrasound image diagnostic apparatus 100, and the shutdown is selectively input in order to, for example, stop ultrasound image diagnostic apparatus 100 for a long time, system control section 11 brings power source control section 12 into the shutdown state. Further, system control section 11 outputs an operation state signal indicating the shutdown state as the operation state of ultrasound image diagnostic apparatus 100 to power supply control section 15.

Power supply control section 15 receives an operation state signal output from system control section 11 and determines that an operation state of ultrasound image diagnostic apparatus 100 has transitioned from the active state to the shutdown state. Further, since AC adapter 50 is not electrically connected to DC input connector 17, (i.e., since an amount of power supplied from DC input connector 17 is less than a predetermined value), power supply control section 15 determines that the power supplied from DC input connector 17 is absent. In accordance with the above determination results, power supply control section 15 causes the power from battery 16 not to be supplied to power source control section 12.

Specifically, power supply control section 15 receives the power supplied from battery 16 and enters the standby state capable of receiving an operation of power button 14 by using the power. After that, for example, termination (shutdown) processing of ultrasound image diagnostic apparatus 100 is performed according to system control section 11.

As described above, the power consumption of power source control section 12 is larger than the power consumption of power supply control section 15. In other words, the power consumption of power supply control section 15 is less than the power consumption of power source control section 12. Accordingly, in the shutdown state of ultrasound image diagnostic apparatus 100, supplying no power to power source control section 12 by stopping the supply of power from battery 16 at power supply control section 15 enables reducing the amount of the standby power to be supplied to power source control section 12 and thereby reducing the power consumption of battery 16, compared with a conventional technology. Thus, for example, even when the standby power is continuously supplied to power supply control section 15 during the Friday night on weekends to the Monday morning in the shutdown state of ultrasound image diagnostic apparatus 100, an amount of the power consumption of the battery is small, and an amount of a remaining charge amount is also small. Consequently, in a case where a medical examination using ultrasound image diagnostic apparatus 100 is performed on the Monday morning, it is possible to prevent the power of battery 16 from running out during the course of the examination.

As described in detail above, in the present embodiment, ultrasound image diagnostic apparatus 100 includes: power source control section 12 that supplies power to power source section 13 which performs supply of power to each section of ultrasound image diagnostic apparatus 100; battery 16 that supplies the power to power source control section 12; DC input connector 17 (an external power supply) that supplies, to power source control section 12, the power supplied from outside of ultrasound image diagnostic apparatus 100; and power supply control section 15 that controls supply of power from battery 16 and DC input connector 17 to power source control section 12 based on an operation state of ultrasound image diagnostic apparatus 100 and the presence or absence of the power supplied from DC input connector 17.

According to the present embodiment with such a configuration, supply of power from battery 16 and DC input connector 17 to power source control section 12 is controlled based on an operation state of ultrasound image diagnostic apparatus 100 and the presence or absence of the power supplied from DC input connector 17. In particular, in a case where the operation state of ultrasound image diagnostic apparatus 100 is the shutdown state, and the power supplied from DC input connector 17 is absent, power supply control section 15 does not supply the power from battery 16 to power source control section 12. That is, in the shutdown state of ultrasound image diagnostic apparatus 100, the power is not supplied to power source control section 12 by stopping the supply of power from battery 16 at power supply control section 15 having the smaller power consumption than power source control section 12. This enables reducing the amount of the standby power to be supplied to power source control section 12 and thereby reducing the power consumption of battery 16, compared with a conventional technology in which the power is supplied from a battery to a power source control section.

Although embodiments of the present invention have been described and illustrated in detail, the disclosed embodiments are made for purpose of illustration and example only and not limitation. The scope of the present invention should be interpreted by terms of the appended claims.

What is claimed is:
1. An ultrasound image diagnostic apparatus, comprising:
   a power source controller that supplies power to a power source which performs supply of power to each part of the ultrasound image diagnostic apparatus;
   a battery that supplies the power to the power source controller;

an external power supply that supplies, to the power source controller, the power supplied from outside of the ultrasound image diagnostic apparatus; and a power supply controller that controls supply of power from the battery and the external power supply to the power source controller based on an operation state of the ultrasound image diagnostic apparatus and a presence or absence of the power supplied from the external power supply, wherein power consumption of the power source controller is larger than power consumption of the power supply controller.

2. The ultrasound image diagnostic apparatus according to claim 1, wherein
the power supply controller operates on receiving the supply of power from the battery or the external power source supply.

3. The ultrasound image diagnostic apparatus according to claim 1, wherein
the power supply controller determines the presence or absence of the power supplied from the external power supply.

4. The ultrasound image diagnostic apparatus according to claim 1, wherein
the power supply controller causes the power from the external power supply to be supplied to the power source controller in a case where the operation state is an active state, and the power supplied from the external power supply is present.

5. The ultrasound image diagnostic apparatus according to claim 4, wherein
the power supply controller charges the battery by supplying, to the battery, the power supplied from the external power supply.

6. The ultrasound image diagnostic apparatus according to claim 1, wherein
the power supply controller causes the power from the battery to be supplied to the power source controller in a case where the operation state is an active state, and the power supplied from the external power supply is absent.

7. The ultrasound image diagnostic apparatus according to claim 1, wherein
the power supply controller causes the power from the battery to be supplied to the power source controller in a case where the operation state is a standby state, and the power supplied from the external power supplier is absent.

8. The ultrasound image diagnostic apparatus according to claim 1, wherein
the power supply controller causes the power from the battery not to be supplied to the power source controller in a case where the operation state is a shutdown state, and the power supplied from the external power supplier is absent.

9. A power supply control method for an ultrasound image diagnostic apparatus, the ultrasound image diagnostic apparatus including: a power source controller that supplies power to a power source which performs a power supply to each part of the ultrasound image diagnostic apparatus; a battery that supplies the power to the power source controller; and an external power supply that supplies, to the power source controller, the power supplied from outside of the ultrasound image diagnostic apparatus, the power supply control method comprising: controlling, by a power supply controller, supply of power from the battery and the external power supply to the power source controller based on an operation state of the ultrasound image diagnostic apparatus and a presence or absence of the power supplied from the external power supply, wherein power consumption of the power source controller is larger than power consumption of the power supply controller.

* * * * *